United States Patent [19]

Kosley et al.

[11] Patent Number: 4,654,336

[45] Date of Patent: Mar. 31, 1987

[54] ETHANOBENZAZEPINES

[75] Inventors: Jr. Kosley, Bridgewater, N.J.; Bernhard Seuring, Hofheim, Fed. Rep. of Germany

[73] Assignee: Hoechst-Roussel Pharmaceuticals Inc., Somerville, N.J.

[21] Appl. No.: 725,853

[22] Filed: Apr. 22, 1985

[51] Int. Cl.[4] .................. C07D 471/08; C07D 491/18; A61K 31/435

[52] U.S. Cl. .................................... 514/214; 540/581; 546/16; 546/216; 546/225; 546/226

[58] Field of Search ...................... 260/244.4; 514/214

[56] References Cited

U.S. PATENT DOCUMENTS 4,021,564  3/1977  Hernestam et al. ................. 514/327

OTHER PUBLICATIONS

Duncan, Jr., J. Med. Chem., 13, 1, (1970).
Fisher, et al., European Journal of Pharmacology, 37, 329, (1976).
Walter, et al., Chem. Abstracts, vol. 82, (1975), entry 164804j.
Mitsuhashi, et al., Chem. Abstracts, vol. 71, (1969), entry 12977c.

Primary Examiner—Donald G. Daus
Assistant Examiner—William A. Teoli, Jr.
Attorney, Agent, or Firm—Raymond R. Wittekind

[57] ABSTRACT

Novel ethanobenzazepines, processes for the preparation thereof, and a method of alleviating pain utilizing compounds or compositions thereof are disclosed.

19 Claims, No Drawings

ETHANOBENZAZEPINES

The present invention relates to ethanobenzazepines. More particularly, the present invention relates to ethanobenzazepines of the formula

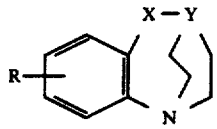

wherein R is hydrogen, halogen or lower alkyl; X is C=O or CHOH; Y is COH or a group of the formula COCOR$^1$ wherein R$^1$ is lower alkyl; and X and Y taken together with their common bond form a group of the formula

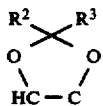

wherein R$^2$ and R$^3$ are independently hydrogen, lower alkyl or phenyl; an optical or geometric isomer thereof, or a pharmaceutically acceptable acid addition salt thereof, which are useful for alleviating pain alone or in combination with inert adjuvants.

Subgeneric to the ethanobenzazepines of the present invention are compounds wherein:

(a) X is C=O; and Y is COH or a group of the formula COCOR$^1$ wherein R$^1$ is loweralkyl;

(b) X is CHOH; Y is COH; and (c) X and Y taken together with their common bond form a group of the formula

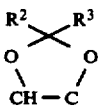

wherein R$^2$ and R$^3$ are independently hydrogen, lower alkyl or phenyl.

The present invention also relates to 4-(2-fluorobenzoyl)piperidines of the formula

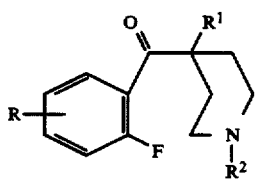

wherein R is hydrogen, halogen or lower alkyl; R$^1$ is hydrogen, bromo or hydroxy; R$^2$ is hydrogen or a group of the formula COR$^3$ wherein R$^3$ is lower alkyl, and 1-oxa-6-azaspiro[2,5]octanes of the formula

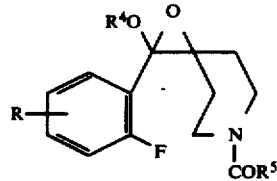

wherein R is hydrogen, halogen or lower alkyl; and R$^4$ and R$^5$ are lower alkyl, as intermediates for the preparation of the present ethanobenzazepines.

As used through the specification and appended claims, the term "alkyl" refers to a straight or branched chain hydrocarbon radical containing no unsaturation and having 1 to 8 carbon atoms such as methyl, ethyl, 1-propyl, 2-propyl, 1-butyl, 1-pentyl, 2-pentyl,3-hexyl, 4-heptyl, 2-octyl, and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy, octoxy, and the like; the term "alkanol" refers to a compound formed by a combination of an alkyl group and a hydroxy radical. Examples of alkanols are methanol, ethanol, 1- and 2-propanol, 2,2-dimethylethanol, hexanol, octanol, and the like. The term "alkanoic acid" refers to a compound formed by combination of a carboxyl group with a hydrogen atom or alkyl group. Examples of alkanoic acids are formic acid, acetic acid, propionic acid, butanoic acid, pentanoic acid, hexanoic acid, octanoic acid, and the like; the term "halogen" refers to a member of the family consisting of fluorine, bromine or iodine. The term "alkanone" refers to a compound formed by the combination of a carbonyl group and two alkyl groups. Examples of alkanones are acetone, 2-butanone, 3-pentanone, 3-hexanone, 2-octanone, and the like. The term "alkanal" refers to a compound formed by the combination of a carbonyl group, an alkyl group and a hydrogen atom. Examples of alkanals are formaldehyde, acetaldehyde, propanal, pentanal, hexanal, octanal, and the like. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of diasteromeric salts of those instant compounds characterized by the presence of a basic amino group and an optically active acid, or by the synthesis from optically active precursors.

The present invention comprehends all optical isomers and racemic forms thereof and all geometric isomers of the compounds disclosed and claimed herein. The formulas of the compounds shown herein are intended to encompass all possible geometric and optical isomers of the compounds so depicted.

The novel ethanobenzazepines of the present invention are prepared by the processes illustrated in the Reaction Scheme.

To prepare the parent ethanobenzazepine system, i.e., a 1,4-ethano-4-hydroxy-2,3,4,5-tetrahydro-5H-1-benzazepin-5-one 12 wherein R is as hereinbeforedescribed, a 2-fluorobenzoyl-4-hydroxypiperidine 11 wherein R is as hereinbeforedescribed, the synthesis of which is hereinafterdescribed, is cyclized in a suitable solvent in the presence of an acid acceptor to afford a compound of formula 12. Among suitable solvents there may be mentioned lower alkylalkanotes such as methyl acetate, ethyl acetate, ethyl propionate, n-butyl acetate and the like, and dipolar aprotic solvents such as dimethylacetamide, dimethylformamide, hexamethylphosphoramide, dimethylsulfoxide and the like, alone or in combination. A combination of n-butyl acetate and dimethylformamide is preferred. Acid acceptors include alkali metal carbonates and bicarbonate, e.g., sodium and potassium carbonate and sodium and potassium bicarbonates, potassium carbonate being preferred. The temperature at which the cyclization is performed is not narrowly critical. To facilitate the cyclization, the reaction is conveniently carried out at a temperature within the range of about 50° C. to the reflux temperature of the reaction medium being preferred. A promotor such as sodium or potassium iodide may be employed, also to facilitate the cyclization. Potassium iodide is preferred.

To prepare an alkanoyl derivative 15 wherein R and $R^1$ are as hereinbeforedescribed of the ketol 12, the ketol 12 is acylated with an alkanoic acid of the formula $R^1CO_2H$ wherein $R^1$ is the hereinbeforedescribed or the anhydride thereof of the formula $(R^1CO)_2O$ in an appropriate solvent in the presence of a base. Appropriate solvents include halocarbons such as dichloromethane, trichloromethane, dichloroethane and the like. Bases include tertiary amines such as trimethyl-, triethyl-, tri-n-butylamine, pyridine, lutidine, s-collidine, quinoline, and the like. Dichloromethane and triethylamine are the preferred solvent and base, respectively. A catalytic amount of a 4-dialkylaminopyridine, e.g., 4-dimethylaminopyridine, may be utilized to promote the conversion. The acylation proceeds readily at about ambient temperature. Elevated reaction temperatures within the range of about 30° to about 80° C. may be employed, however, to facilitate the conversion.

To synthesize a diol of formula 13 wherein R is as hereinbeforedescribed, the ketol 12 is reduced with an alkali metal borohydride, for example, lithium, sodium or potassium borohydride, in an alkanol such as methanol, ethanol, 2-propanol and the like, or an alkali metal aluminum hydride, for example, lithium aluminum hydride, in an ethereal solvent such as diethyl ether, di-isopropyl ether, dimethoxyethane, dioxane and tetrahydrofuran, alone or in combination. Sodium borohydride and a combination of methanol and tetrahydrofuran are the preferred reducing agent and solvent systems, respectively. The reduction is conveniently accomplished at about ambient temperature. Higher reduction temperatures within the range of about 25° to the reflux temperature of the reaction medium may be employed to promote the reduction.

To elaborate the dioxolo function, i.e., to prepare a compound of formula 14 wherein R, $R^2$ and $R^3$ are as hereinbefore defined, a diol 13 is treated with an alkanal of the formula $R^2$-CHO, an alkanone of the formula $R^2R^3CO$ wherein $R^2$ and $R^3$ are as hereinbeforedefined, or the acetal or ketal derivatives of the formula $R^2CH(OR^5)_2$ wherein $R^5$ is lower alkyl, in an ethereal solvent such as diethyl ether, di-isopropyl ether, 1,2-dimethoxyethane, tetrahydrofuran and dioxane, preferably tetrahydrofuran, in the presnece of a mineral acid such as sulfuric acid, an aromatic sulfonic acid such as p-toluene sulfonic acid, or a Lewis acid such as boron trifluoride etherate, preferably boron trifluoride etherate, at a reaction temperature within the range of about 15° to 65° C., preferably at about ambient temperature.

The 2-fluorobenzoyl-4-hydroxypiperidine 11, the precursor for the fabrication of the ethanobenzazepines of the present invention are prepared from readily available starting materials according to the conventional processes depicted in the Reaction Scheme.

Thus condensation of the fluorobenzene 2 wherein R is as hereinbeforedefined with a 1-alkanoyl-4-piperidine carbonyl halide 3, the preparation of which is described in R. L. Duncan, et al., J. Med. Chem., 13, 1 (1970), wherein $R^4$ is as hereinbeforedefined and Hal is bromo or chloro in the presence of a Friedel-Crafts catalyst such as aluminum chloride at the reflux temperature of the reaction medium affords a 4-(2-fluorobenzoyl)-piperidine 4 wherein R and $R^4$ are as definedhereinbefore, which is halogenated by means of bromine, in an alkanoic acid such as acetic acid at a reduced temperature within the range of about 10° to 30° C., a temperature range of about 10°-12° C. being preferred, to a 4-bromo-4-(2-fluorobenzoyl)piperidine 5 wherein R and $R^4$ are as defined above and converted to a 2-alkoxy-6-azaspiro[2,5]octane 6 wherein R and $R^4$ are as defined hereinbefore and $R^5$ is lower alkyl with an alkali metal alkoxide such as sodium methoxide in the corresponding alkanol, methanol, at about the reflux temperature of the reaction medium. Rearrangement of a 2-alkoxy-6-azaspiro[2,5]octane 6 with a mineral acid such as hydrochloric acid in an alkanol such as ethanol at about ambient temperature provides a 4-(2-fluorobenzoyl)-4-hydroxypiperidine 10 wherein R and $R^4$ are as described above which is hydrolyzed with a mineral acid, e.g., hydrochloric acid, at about the reflux temperature of the reaction medium to the presursor 11 wherein R and $R^4$ have the meaning hereinbeforedisclosed.

Alternatively, a fluorobenzene 2 is treated with N-methylformanilide 7 in a hydrocarbon-ethereal solvent such as n-hexane-tetrahydrofuran in the presence of an alkylalkali metal such as n-butyllithium at a reduced temperature of about −45° C. to about −60° C. to afford a 2-fluorobenzaldehyde 8 wherein R is as definedhereinbefore which is silyated with trimethylsilylcyanide in the presence of a Lewis acid such as, for example, zinc iodide, at a temperature within the range of about 65° to about 95° C. to provide a trimethylsilyl-2-fluorobenzaldehyde cyanohydrin 9 wherein R is as hereinbeforedefined and condensed with a 1-alkanoyl-4-piperidine of the formula

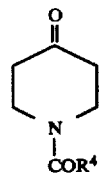

wherein $R^4$ is as defined above, in a hydrocarbon-ether solvent, e.g., n-hexane-tetrahydrofuran, in the presence of an alkali metal dialkylamide such as lithiumdiisopropylamide at a reduced temperature within the range of about −80° to about −20° C. to afford a 1-alkanoyl-4-(2-fluorobenzyl)-4-hydroxypiperidine 10. Hydrolysis of 10 by the process described above provides the precursor 11 for the preparation of the instant 1,4-ethano-1,2,3,4-tetrahydrobenzazepines.

The 1,4-ethanobenzazepines of the present invention are useful as analgetics due to their ability to alleviate pain in mammals. The analgetic utility is demonstrated in the phenyl-p-quinone writhing assay in mice, a standard assay for analgetic activity [Proc. Soc. Exptl.Biol med., 95 729 (1957)]. Thus, for instance, at a subcutaneous dose of 20 mg/kg the percent decrease in writhes in mice produced in this assay is as shown in the Table.

TABLE

| Compound | Dose (mg/kg) | Analgetic Activity % Decrease in Writhes |
|---|---|---|
| 1,4-ethano-4,5-dihydroxy-2,3,4,5-tetrahydro-1H—1-benzazepine | 20 | 48 |
| 4-acetoxy-1,4-ethano-2,3,4,5-tetrahydro-5H—1-benzazepin-5-one | 20 | 62 |
| 9-fluoro-3a,4,5,10b-tetrahydro-2,2-dimethyl-3a,6-ethano-1,3-dioxolo[4,5-d][1]benzazepine | 20 | 25 |
| 3a,4,5,10b-tetrahydro-2-ethyl-3a,6-ethano-1,3-dioxolo[4,5-d][1]benzazepine | 20 | 52 |
| 3a,4,5,10b-tetrahydro-2-phenyl-3a,6-ethano-1,3-dioxolo[4,5-d][1]benzazepine | 20 | 42 |
| 9-fluoro-3a,4,5,10b-tetrahydro-2-phenyl-3a,6-ethano-1,3-dioxolo[4,5-d][1]benzazepine | 20 | 25 |
| propoxyphene (standard) | 3.9 | 50 |
| pentazocine (standard) | 1.3 | 50 |

Analgesia production is achieved when the present ethanobenzazepines are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood tht the dosages set forth herein are exemplary only and that they do not, to any extent, limit the scope or practice of the invention.

Effective amounts of the compounds of the present invention may be administered to a subject by any one of the several methods, for example, orally as in capsules or tablets, parenterally in the form of sterile solutions or suspensions, and in some cases intravenously in the form of sterile solutions. The 1,4-ethanobenzazepines of the present invention, while effective themselves, may be formulated and administered in the form of their pharmaceutically acceptable addition salts for purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

Effective quantities of the compounds of the invention may be administered orally, for example, with an inert diluent or with an edible carrier. They may be enclosed in gelatin capsules or compressed into tablets. For the purposes of oral therapeutic administration, the aforesaid compounds may be incorporated with an excipient and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0–300 milligrams of the active compound.

The tablets, pills, capsules, troches and the like may also contain the following ingredients: a binder such as microcrystalline cellulose, gum tragacanth or gelatine; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin, or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parentereal preparation can be enclosed in ampules, disposable syringes or multiple dose vials made of glass or plastic. The following examples are for illustrative purposes only and are not to be construed as limiting the invention.

EXAMPLE 1

1-Acetyl-4-(2,5-difluorobenzoyl)piperidine

To a stirred suspension of 100 g of 1-acetyl-4-piperidine carboxylic acid chloride in 500 ml of 1,4-difluorobenzene was added in aliquots, 211 g of anhydrous aluminum chloride. The mixture was stirred at reflux under nitrogen for 3 hrs and allowed to cool to room temperature. The mixture was poured into ice and extracted twice with ethyl acetate. The extracts were washed with saturated sodium bicarbonate solution and dried over anhydrous potassium carbonate. Filtration followed by evaporation of the solvent provided an oil which crystallized on standing. The solid was washed with cyclohexane and dried to provide 73.3 g (52.1%) of 1-acetyl-4-(2,5-difluorobenzoyl)piperidine: mp 82°–87° C. Recrystallization from a mixture of isopropyl alcohol, diisopropyl ether and hexane provided product with mp 93°–95° C.

| ANALYSIS: | | | |
|---|---|---|---|
| Calculated for $C_{16}H_{15}F_2NO_2$: | 62.81% C | 5.66% H | 5.24% N |
| Found: | 62.82% C | 5.75% H | 5.26% N |

EXAMPLE 2

1-Acetyl-4-(2,5-difluorobenzoyl)-4-bromopiperidine

To a stirred solution of 11.2 g of 1-acetyl-4-(2,5-difluorobenzoyl)piperidine in 225 ml of glacial acetic acid was added dropwise over 0.5 hr a solution of 13.5 ml (42.1 g) of bromine in 115 ml of glacial acetic acid at a rate such that the temperature remained between 10°–12° C. The mixture was stirred for an additional 10–15 mins, poured into water, extracted twice with ethyl acetate, and the solvent evaporated to provide an oil. The oil was dissolved in ethyl acetate, washed with saturated sodium bicarbonate solution, dried over anhydrous magnesium sulfate, filtered, and the solvent evaporated to provide product as an oil.

EXAMPLE 3

2,5-Difluorobenzaldehyde

To a stirred solution of 194.5 g (1.70 mol) of 1,4-difluorobenzene in 2 of dry tetrahydrofuran at −60° C. was added dropwise over 45 mins 1.70 mol (2.2M in hexane) of n-butyllithium at a rate such that the temperature remained below −55° C. The reaction mixture was stirred for 45 mins at below −50° C. and 1.5 hr at −50° to −45° C. The solution was then cooled to −60° C. and a solution of 230 g of N-methylformanilide in 300 ml of tetrahydrofuran was added dropwise over 30 mins. The mixture was stirred for 1 hr at −50° C. and allowed to warm to −30° C. over 15 mins. The mixture was then poured into ice water, neutralized (pH 6–7) with 10% sulfuric acid and extracted three times with hexane. The extracts were washed once with 1N sulfuric acid, once with saturated sodium chloride solution and concentrated to an oil. Distillation at 64°–65° C. (20 mm) provided 187.5 g (77.5%) of product.

EXAMPLE 4

α-(Trimethylsilyloxy)-2,5-difluorobenzeneacetonitrile

To 25.0 g of trimethylsilylcyanide was added a large spatula of zinc iodide. To the stirred mixture was added dropwise 32.6 g of 2,5-difluorobenzaldehyde with external cooling at a rate such that the temperature rose to 65° C. The mixture was stirred 4 hr at 95° C. Distillation at 75° (0.1 mm) provided 41.2 g (75.6%) of product.

EXAMPLE 5

1-Acetyl-4-(2,5-difluorobenzoyl)-4-hydroxypiperidine

To a stirred solution of sodium methoxide, prepared from 3.54 g of sodium spheres in 110 ml dry (3A molecular sieves) methanol, was added dropwise a solution of 9.56 g of 1-acetyl-4-bromo-(2,5-difluorobenzoyl)piperidine in 20 ml of methanol. The solution was stirred at reflux for 1 hr, allowed to cool to room temperature, poured into ice-water, extracted twice with ether and the extracts were dried over anhydrous potassium carbonate. Filtration followed by evaporation of the solvent provided 6.4 g of 6-acetyl-2-(2,5-difluorophenyl)-2-methoxy-6-azaspiro[2,5]octane as an oil.

To 6.4 g of 6-acetyl-2-(2,5-difluorophenyl)-2-methoxy-1-oxa-6-azaspiro[2,5]octane was added a solution of 8.1 ml of conc hydrochloric acid in 42 ml of ethanol. The mixture was stirred at room temperature for 15 mins, poured into ice-water and extracted twice with ethyl acetate. The extracts were washed with saturated sodium bicarbonate solution, saturated sodium chloride solution and dried over anydrous potassium carbonate. Filtration followed by evaporation of solvent provided 4.70 g of an oil which crystallized on drying under vacuum for 48 hrs. Recrystallization from ethyl acetate provided 3.11 g (40%) of 1-acetyl-4-(2,5-difluorobenzoyl)-4-hydroxy-piperidine, mp 118°–120° C.

| ANALYSIS: | | | |
|---|---|---|---|
| Calculated for $C_{14}H_{15}F_2NO_3$: | 59.36% C | 5.34% H | 4.95% N |
| Found: | 59.04% C | 5.45% H | 4.85% N |

EXAMPLE 6

4-(2,5-Difluorobenzoyl)-4-hydroxypiperidine

A suspension of 5.66 g of 1-acetyl-4-(2,5-difluorobenzoyl)-4-hydroxypiperidine in 10 ml of 6N hydrochloric acid was stirred at reflux, under nitrogen for 3.5 hrs. The reaction mixture was allowed to cool to 0° C. whereupon a solid separated. The solid was collected, washed with ice-cold acetone and dried to give 4.4 g (80%) of product, mp 191°–193° C.

| ANALYSIS: | | | |
|---|---|---|---|
| Calculated for $C_{12}H_{13}F_2NO_2.HCl$: | 51.90% C | 5.08% H | 5.04% N |
| Found: | 51.76% C | 4.99% H | 4.96% N |

EXAMPLE 7

1-Acetyl-4-(2-fluorobenzoyl)-4-hydroxypiperidine

A solution of lithiumdiisopropylamide in tetrahydrofuran was prepared, under nitrogen, by addition of 181 ml of 2.2N solution of n-butyllithium in hexane to a solution of 56 ml of diisopropylamine in ca. 400 ml of dry tetrahydrofuran (freshly distilled from lithium aluminumhydride) at −70° C. and subsequent warming up to −20° C. The lithiumdiisopropylamide solution was then cooled to −74° C. and 85 g of α-(trimethylsilyloxy)-2-fluorobenzeneacetonitrile were added dropwise so that the temperature remained between −74° C.

and −70° C. The resulting solution was stirred for 1 hr at −74° C. A mixture of 53.6 g of 1-acetyl-4-piperidone and 60 ml of tetrahydrofuran was then added at −70° C. to −60° C. The resulting mixture was allowed to warm up very slowly (ca. 20 hrs) to 0° C. After stirring for two additional hrs at 0° C., the mixture was poured into a stirred mixture of 0.5 l of sat ammonium chloride solution, 0.5 kg of ice and 1 liter of ethyl acetate. The layers were separated and the aqueous layer extracted twice with ethyl acetate. The combined organic layers were washed with dilute potassium carbonate solution, brine, dried over anhydrous potassium carbonate, filtered, and evaporated to provide 114 g (89%) of 1-acetyl-4-(2-fluorobenzoyl)-4-trimethylsilyloxypiperidine as a resin. The resin was dissolved in 600 ml of methanol and 600 ml of 1.2N hydrochloric acid was added with vigorous stirring. Stirring was continued for 20 hrs at room temperature. The resulting solution was stirred into brine and extracted thrice with ethyl acetate. The extracts were washed with dilute potassium carbonate solution, dried over anhydrous sodium sulfate and evaporated, finally at high vacuum, to yield a solid. Trituration with hot ethyl acetate provided 29.4 g of analytically pure product, mp 144°–146° C. From the mother liquor another 28.1 g of product was obtained by addition of hexane. Total yield 57.5 g (57%).

ANALYSIS:

| Calculated for $C_{14}H_{16}FNO_3$: | 63.38% C | 6.08% H | 5.28% N |
|---|---|---|---|
| Found: | 63.22% C | 6.32% H | 5.24% N |

EXAMPLE 8

4-(2-Fluorobenzoyl)-4-hydroxypiperidine

A mixture of 13.3 g of 1-acetyl-4-(2-fluorobenzoyl)-4-hydroxypiperidine and 20 ml of 6N hydrochloric acid was stirred at reflux under nitrogen for 4 hrs. The reaction mixture was allowed to cool and poured onto ca. 100 g of ice. Methylene chloride was added, and the separated aqueous layer was made strongly basic by means of 15% sodium hydroxide solution. The aqueous layer was extracted three times with 80 ml of methylene chloride. The extracts were dried over anhydrous potassium carbonate, filtered and evaporated provide anhydrous 9.5 g (85%) of product, mp 133°–135° C.

ANALYSIS:

| Calculated for $C_{12}H_{14}FNO_2$: | 64.56% C | 6.32% H | 6.28% N |
|---|---|---|---|
| Found: | 64.25% C | 6.23% H | 6.26% N |

EXAMPLE 9

1,4-Ethano-4-hydroxy-2,3,4,5-tetrahydro-1H-1-benzazepine-5-one

A mixture of 11.0 g of 4-(2-fluorobenzoyl)-4-hydroxypiperidine, 10.1 g of milled anhydrous potassium carbonate, 330 ml of n-butyl acetate and 20 ml of dimethylformamide was stirred at reflux under nitrogen for ca. 26 hrs. The hot reaction mixture was filtered. The filter cake was washed with hot chloroform and the filtrates evaporated to yield a solid. Recrystallization from ethyl acetate provided 9.0 g (90%) of product, mp 134°–136° C.

ANALYSIS:

| Calculated for $C_{12}H_{13}NO_2$: | 70.91% C | 6.46% H | 6.89% N |
|---|---|---|---|
| Found: | 70.85% C | 6.52% H | 6.92% N |

EXAMPLE 10

1,4-Ethano-7-fluoro-4-hydroxy-2,3,4,5-tetrahydro-1H-1-benzazepine-5-one

A suspension of 9.86 g of 4-(2,5-difluorobenzoyl)-4-hydroxypiperidine, 250 ml of n-butyl acetate, 16.3 g of anhydrous potassium carbonate and 0.9 g of potassium iodide was stirred at reflux for 40 hrs. The mixture was allowed to cool to room temperature and poured into ice water. The mixture was extracted twice with ether, washed with water and saturated sodium chloride solution and dried over anhydrous potassium carbonate. Filtration followed by evaporation of the solvent provided an oil. The oil was filtered through alumnia (eluent:ether). Evaporation of solvent provided on oil which was further purified by high pressure liquid chromatography using a Waters Prep 500 apparatus (eluent: 3% methanol-dichloromethane). Concentration provided 5.33 g (58.9%) of 1,4-ethano-7-fluoro-4-hydroxy-2,3,4,5-tetrahydro-5H-1-benzazepin-5-one, mp 102°–104° C.

ANALYSIS:

| Calculated for $C_{12}H_{12}FNO_2$: | 65.15% C | 5.43% H | 6.33% N |
|---|---|---|---|
| Found: | 65.12% C | 5.48% H | 6.13% N |

EXAMPLE 11

1,4-Ethano-4,5-dihydroxy-1,2,3,4-tetrahydro-5H-1-benzazepine

Sodium borohydride (1.2 g) was added to a stirred solution of 4.06 g of 1,4-ethano-4-hydroxy-2,3,4,5-tetrahydro-5H-1-benzazepine-5-one in a mixture of 50 ml of methanol and 10 ml of tetrahydrofuran at room temperature. The reaction mixture was stirred overnight at ambient temperature and evaporated to dryness. The residue was treated with 150 ml of almost saturated potassium carbonate solution and the resulting mixture extracted with ca. 300 ml of chloroform by means of continuous extraction for 20 hrs. The extract was dried over anhydrous sodium sulfate and the solvent evaporated to give 4.5 g of a solid. Recrystallization from chloroform-hexane provided 2.7 g (66%) of 1,4-ethano-4,5-dihydroxy-2,3,4,5-tetrahydro-5H-1-benzazepine, mp 169°–170° C.

ANALYSIS:

| Calculated for $C_{12}H_{15}NO_2$: | 70.22% C | 7.37% H | 6.83% N |
|---|---|---|---|
| Found: | 70.01% C | 7.32% H | 6.75% N |

EXAMPLE 12

1,4-Ethano-4,5-dihydroxy-7-fluoro-2,3,4,5-tetrahydro-1H-1-benzazepine

Sodium borohydride powder (1.7 g) was added in one portion to a stirred solution of 5.1 g of 1,4-ethano-7-fluoro-4-hydroxy-2,3,4,5-tetrahydro-1H-1-benzazepine-5-one in a mixture of 80 ml of methanol and 5 ml of tetrahydrofuran. The reaction mixture was stirred overnight at room temperature, made strongly acidic by dropwise addition of concentrated hydrochloric acid and evaporated to dryness. The residue was stirred with excess potassium carbonate solution and the cloudy mixture extracted twice with ethyl acetate. The organic layers were washed with brine, dried over anhydrous sodium sulfate, filtered and evaporated to yield a solid. Recrystallization from ca. 30 ml of chloroform provided 2.6 g (51%) of product, mp 138°–140° C.

ANALYSIS:

| | | | |
|---|---|---|---|
| Calculated for $C_{12}H_{14}FNO_2$: | 64.56% C | 6.32% H | 6.28% N |
| Found: | 64.67% C | 6.30% H | 6.27% N |

EXAMPLE 13

4-Acetoxy-1,4-ethano-2,3,4,5-tetrahydro-1H-1-benzazepine-5-one

A suspension of 4.06 g of 4-hydroxy-1,4-ethano-2,3,4,5-tetrahydro-1H-1-benzazepine-5-one and 0.5 g of 4-dimethylaminopyridine in 15 ml of dry dichloromethane was prepared under nitrogen. Triethylamine (3.03 g) was added followed by addition of 4.3 g of acetic anhydride. The reaction mixture was stirred overnight at ambient temperature under nitrogen. The solvent was evaporated under reduced pressure, and the residue was dissolved in a mixture of dichloromethane and methanol. Purification of the desired product by means of flash chromatography (silica gel, 1% methanol-dichloromethane) gave an oil. Treatment with hexane-diisopropylether provided, after cooling and seeding, 3.0 g (61%) of product, mp 88°–90° C.

ANALYSIS:

| | | | |
|---|---|---|---|
| Calculated for $C_{14}H_{15}NO_3$: | 68.56% C | 6.16% H | 5.71% N |
| Found: | 68.78% C | 6.35% H | 5.66% N |

EXAMPLE 14

4-Acetoxy-1,4-ethano-7-fluoro-2,3,4,5-tetrahydro-1H-1-benzazepine-5-one

A mixture of 4.42 g of 4-hydroxy-1,4-ethano-7-fluoro-2,3,4,5-tetrahydro-1H-1-benzazepine-4-one, 0.5 g of 4-dimethylaminopyridine and 17 ml of dry dihloromethane was prepared under nitrogen. Triethylamine (3.03 g) and 4.3 g of acetic acid were added at room temperature. The resultant solution was stirred overnight at room temperature under nitrogen. Removal of solvent under reduced pressure and separation of the desired product by means of flash chromatography on silica gel (1% methanol-dichloromethane) provided a solid. Recrystallization from diisopropyl ether provided 3.6 g (68.4%) of product, mp 135°–136° C.

ANALYSIS:

| | | | |
|---|---|---|---|
| Calculated for $C_{14}H_{14}FNO_3$: | 63.87% C | 5.36% H | 5.32% N |
| Found: | 64.01% C | 5.51% H | 5.23% N |

EXAMPLE 15

3a,4,5,10b-Tetrahydro-2-methyl-3a,6-ethano-1,3-dioxolo[4,5-d][1]benzazepine maleate To a stirred mixture of 4.1 g of 1,4-ethano-4,5-dihydroxy-2,3,4,5-tetrahydro-5H-1-benzazepine 50 ml of anhydrous tetrahydrofuran and 5 ml of acetaldehyde was added 3.0 ml of boron trifluoride etherate under nitrogen. An additional 8 ml of acetaldehyde diethylacetal and 3 ml of boron trifluoride etherate was added, and the solution was stirred for one day at room temperature. The reaction mixture was poured into an excess of a half saturated aqueous potassium carbonate solution. Extraction with ether, drying of the organic layers over anhydrous sodium sulfate, evaporation of solvent and purification of the oil by means of flash chromatography (silica gel, 3% methanol-dichloromethane/0.1% aqueous ammonia, eluent) gave 3.8 g (82%) of product as the free base. A 3.5 g portion of the free base was dissolved in ether and a stochiometric amount of an ethereal solution of maleic acid was added. Filtration, washing with ether and drying under high vacuum provided 3.9 g (56%) of product, mp 134°–137° C.

ANALYSIS:

| | | | |
|---|---|---|---|
| Calculated for $C_{18}H_{21}NO_6$: | 62.24% C | 6.09% H | 4.03% N |
| Found: | 62.51% C | 6.20% H | 3.92% N |

EXAMPLE 16

3a,4,5,10b-Tetrahydro-2-ethyl-3a,6-ethano-1,3-dioxolo[4,5-d][1]benzazepine hydrochloride A mixture of 3.08 g of 1,4-ethano-4,5-dihydroxy-2,3,4,5-tetrahydro-5H-1-benzazepine, 50 ml of anhydrous tetrahydrofuran, 7 ml of propionaldehyde diethylacetal and 5.2 ml of boron trifluoride etherate was stirred under nitrogen for 2 hrs at room temperature and for 1.5 hrs at 40° C. The reaction mixture was poured into excess ice-cold aqueous potassium carbonate solution and extracted twice with a mixture of ether and ethyl acetate. The extracts were washed with brine, dried and evaporated to give an oil. Purification by means of flash chromatography provided 2.1 g (57%) of product as an oil. The hydrochloride was prepared by dissolving the oil in anhydrous ether and adding dropwise ethereal hydrochloric acid. Filtration and drying yielded 2.1 g (50%) of product, mp 235°–237° C. (dec).

ANALYSIS:

| | | | |
|---|---|---|---|
| Calculated for $C_{15}H_{20}ClNO_2$: | 63.94% C | 7.15% H | 4.97% N |
| Found: | 64.22% C | 7.38% H | 4.63% N |

EXAMPLE 17

3a,4,5,10b-Tetrahydro-2,2-dimethyl-3a,6-ethano-1,3-dioxolo[4,5-d][1]benzazepine

To a solution of 3.08 g of 1,4-ethano-4,5-dihydroxy-2,3,4,5-tetrahydro-5H-1-benzazepine in a mixture of 50 ml of dry tetrahydrofuran and 4 ml of 2,2-dimethoxypropane was added 3.7 ml of distilled boron trifluoride ethereate dropwise with vigorous stirring under an atmosphere of nitrogen. Stirring was continued at room temperature for 2.5 hrs. The reaction mixture was poured into 200 ml of ice cold half-saturated aqueous potassium carbonate solution. Extraction with ether (3x), washing with brine and drying over sodium sulfate and evaporation of solvent provided 3.5 g of a solid. Recrystallization from diisopropyl ether gave 2.5 g (67%) of product, mp 135°–137° C.

| ANALYSIS: | | | |
|---|---|---|---|
| Calculated for $C_{15}H_{19}NO_2$: | 73.44% C | 7.87% H | 5.71% N |
| Found: | 73.95% C | 7.85% H | 5.70% N |

EXAMPLE 18

3a,4,5,10b-Tetrahydro-2-phenyl-3a,6-ethano-1,3-dioxolo[4,5-d][1]benzazepine

A solution of 3.08 g of 1,4-ethano-4,5-dihydroxy-2,3,4,5-tetrahydro-1H-1-benzazepine and 3.04 g of benzaldehyde dimethyl acetal in 50 ml of anhydrous tetrahydrofuran was prepared under nitrogen. Boron trifluoride etherate (3.8 ml) was added with vigorous stirring at 35° C. over a period of a few mins. The reaction mixture was stirred for 2 hrs at 50° C. and then poured into a stirred ice-cold dilute potassium carbonate solution. The product was extracted several times with ether. Drying over anhydrous sodium sulfate and removal of the solvent under reduced pressure provided a solid. Recrystallization from diisopropyl ether yielded 2.4 g (54.5%) of product, mp 144°–146° C.

| ANALYSIS: | | | |
|---|---|---|---|
| Calculated for $C_{19}H_{19}NO_2$: | 77.79% C | 6.53% H | 4.78% N |
| Found: | 77.76% C | 6.71% H | 4.60% N |

EXAMPLE 19

9-Fluoro-3a,4,5,10b-tetrahydro-2-methyl-3a,6-ethano-1,3-dioxolo-[4,5-d][1]benzazepine To a solution of 3.7 g of 1,4-ethano-b 4,5-dihydroxy-7-fluoro-2,3,4,5-tetrahydro-1H-1-benzazepine in 50 ml of dry tetrahydrofuran, 2.2 ml of boron trifluoride etherate was added dropwise, with stirring, at room temperature, under nitrogen. To the mixture, 5 ml of acetaldehyde was added. After stirring for ca. 16 hrs, 1.2 ml of freshly distilled boron trifluoride etherate and of ca. 2 ml of acetaldehyde diethylacetal were added, and the solution was stirred for ca. two hrs at 40° C. The reaction mixture was then stirred into a mixture of 200 ml of saturated sodium bicarbonate solution and a few ml of saturated potassium carbonate solution. Extraction with ethyl ether (twice) and ethyl acetate, washing of the combined organic extracts with brine, drying over anhydrous potassium carbonate and evaporation of the solvent provided 4.8 g of a semi-solid. Purification by means of flash chromatography (silica gel, 1–3% methanol-dichloromethane) followed by recrystallization from hexane-diisopropyl ether gave 1.8 g (44%) of product, mp 103°–107° C.

| ANALYSIS: | | | |
|---|---|---|---|
| Calculated for $C_{14}H_{16}FNO_2$: | 67.45% C | 6.47% H | 5.62% N |
| Found: | 67.55% C | 6.48% H | 5.54% N |

EXAMPLE 20

9-Fluoro-3a,4,5,10b-tetrahydro-2,2-dimethyl-3a,6-ethano-1,3-dioxolo[4,5-d][1]benzazepine To a solution of 2.70 g of 1,4-ethano-4,5-dihydroxy-7-fluoro-2,3,4,5-tetrahydro-1H-1-benzazepine in 40 ml of anhydrous tetrahydrofuran was added 1.6 ml of boron trifluoride etherate with vigorous stirring at room temperature under nitrogen. To the mixture, 2 ml of acetone was added and the mixture stirred for 16 hrs. Boron trifluoride etherate (1.3 ml) was added, followed by 4 ml of 2,2-dimethoxypropane. After stirring for about 30 mins at 35° C., the solution was poured into a mixture of 100 ml of saturated sodium bicarbonate solution, a few ml of saturated potassium carbonate solution and 50 ml of ether. The aqueous layer was washed twice with ether. The ether layers were dried over anhydrous sodium sulfate and evaporated to dryness to give a solid. Recrystallization from hexane-diisopropyl ether provided 2.5 g (79%) of product, mp 120°–122° C.

| ANALYSIS: | | | |
|---|---|---|---|
| Calculated for $C_{15}H_{18}FNO_2$: | 68.42% C | 6.89% H | 5.32% N |
| Found: | 68.45% C | 7.04% H | 5.24% N |

EXAMPLE 21

9-Fluoro-3a,4,5-10b-tetrahydro-2-phenyl-3a,6-ethano-1,3-dioxolo-[4,5-d][1]benzazepine A solution of 3.35 g of 7-fluoro-1,4-ethano-4,5-dihydroxy-2,3,4,5-tetrahydro-1H-1-benzazepine and 3.04 g of benzaldehyde dimethyl acetal in 50 ml of anhydrous tetrahydrofuran was prepared under nitrogen. Boron trifluoride etherate (3.8 ml) was added with vigorous stirring at room temperature over a period of a few mins. The solution was stirred for 2 hrs, poured into a stirred ice-cold dilute potassium carbonate solution, and extracted several times with ether. Drying the ether extracts over anhydrous sodium sulfate and evaporation of the solvent under high vacuum provided an oil, which crystallized on standing. Recrystallization from diisopropyl ether yielded 2.4 g (51%) of product, mp 128°–130° C.

| ANALYSIS: | | | |
|---|---|---|---|
| Calculated for $C_{19}H_{18}FNO_2$: | 73.32% C | 5.83% H | 4.50% N |
| Found: | 73.24% C | 6.00% H | 4.36% N |

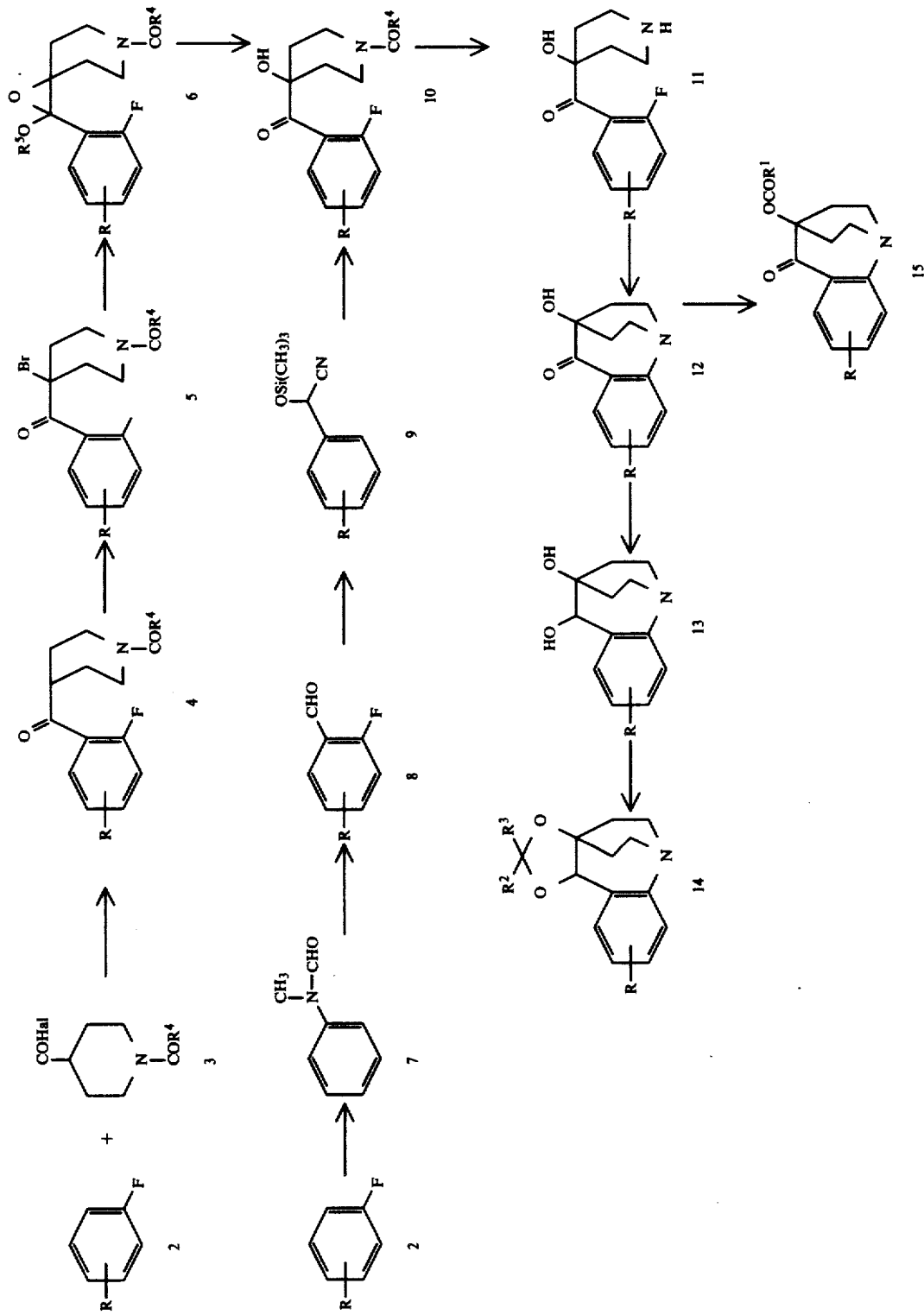
REACTION SCHEME wherein R, R¹, R², R³, R⁴, and R⁵ are as hereinbeforedefined.

We claim:

1. A compound of the formula

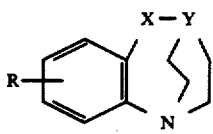

wherein R is hydrogen, halogen or lower alkyl; X is C=O or CHOH; Y is COH or a group of the formula COCOR¹ wherein R¹ is lower alkyl; and X and Y taken together with their common bond form a group of the formula

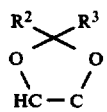

wherein R² and R³ are independently hydrogen, lower alkyl or phenyl; an optical isomer thereof or a pharmaceutically acceptable acid addition salt thereof.

2. A compound of claim 1 wherein X is C=O; and Y is COH or a group of the formula COCOR¹ wherein R¹ is lower alkyl.

3. A compound of claim 1 wherein X is CHOH; and Y is COH.

4. A compound of claim 1 wherein X and Y taken together with their common bond form a group of the formula

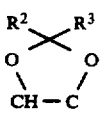

wherein R² and R³ are independently hydrogen, lower alkyl or phenyl.

5. The compound of claim 2 which is 1,4-ethano-4-hydroxy-2,3,4,5-tetrahydro-5H-1-benzazepin-5-one.

6. The comound of claim 2 which is 1,4-ethano-7-fluoro-4-hydroxy-2,3,4,5-tetrahydro-5H-1-benzazepin-5-one.

7. The compound of claim 3 which is 1,4-ethano-4,5-dihydroxy-2,3,4,5-tetrahydro-1H-1-benzazepine.

8. The compound of claim 3 which is 1,4-ethano-4,5-dihydroxy-7-fluoro-2,3,4,5-tetrahydro-1H-1-benzazepine.

9. The compound of claim 2 which is 4-acetoxy-1,4-ethano-2,3,4,5-tetrahydro-5H-1-benzazepin-5-one.

10. The compound of claim 2 which is 4-acetoxy-1,4-ethano-7-fluoro-2,3,4,5-tetrahydro-5H-1-benzazepin-5-one.

11. The compound of claim 4 which is 3a,4,5,10b-tetrahydro-2-methyl-3a,6-ethano-1,3-dioxolo[4,5-d][1]benzazepine.

12. The compound of claim 4 which is 3a,4,5,10b-tetrahydro-2-ethyl-3a,6-ethano-1,3-dioxolo[4,5-d][1]benzazepine.

13. The compound of claim 4 which is 3a,4,5,10b-tetrahydro-2,2-dimethyl-3a,6-ethano-1,3-dioxolo[4,5][1]benzazepine.

14. The compound of claim 4 which is 3a,4,5,10b-tetrahydro-2-phenyl-3a,6-ethano-1,3-dioxolo[4,5][1]benzazepine.

15. The compound of claim 4 which is 9-fluoro-3a,4,5,10b-tetrahydro-2-methyl-3a,6-ethano-1,2-dioxolo[4,5-d][1]benzazepine.

16. The compound of claim 4 which is 9-fluoro-3a,4,5,10b-tetrahydro-2,2-dimethyl-3a,6-ethano-1,3-dioxolo[4,5-d][1]-benzazepine.

17. The compound of claim 4 which is 9-fluoro-3a,4,5,10b-tetrahydro-2-phenyl-3a,6-ethano-1,3-dioxolo[4,5-d][1]benzazepine.

18. A method of alleviating pain comprising administering to a mammal in need of pain alleviation a pain alleviating effective amount of a compound of the formula

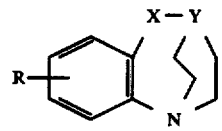

wherein R is hydrogen, halogen or lower alkyl; X is C=O or CHOH; Y is COH or a group of the formula COCOR¹ wherein R¹ is lower alkyl; and X and Y taken together with their common bond form a group of the formula

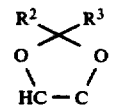

wherein R² and R³ are independently hydrogen, lower alkyl or phenyl; an optical isomer thereof, or a pharmaceutically acceptable acid addition salt thereof.

19. A pain alleviating composition comprising an inert pain alleviating adjuvant and, as the active ingredient, an amount effective in alleviating pain of a compound of the formula

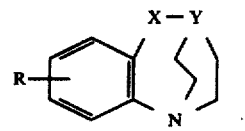

wherein R is hydrogen, halogen or lower alkyl; X is C=O or CHOH; Y is COH or a group of the formula COCOR¹ wherein R¹ is lower alkyl; and X and Y taken together with their common bond form a group of the formula

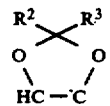

wherein R² and R³ are independently hydrogen, lower alkyl or phenyl; an optical isomer thereof, or a pharmaceutically acceptable acid addition salt thereof.

* * * * *

UNITED STATES PATENT AND TRADEMARK OFFICE
CERTIFICATE OF CORRECTION

PATENT NO. : 4,654,336

DATED : March 31, 1987

INVENTOR(S) : Raymond W. Kosley, Jr. and Bernhard Seuring

It is certified that error appears in the above-identified patent and that said Letters Patent is hereby corrected as shown below:

Column 3, line 66 - "presnece" should be -- presence --

Column 6, line 63 - "parentereal" should be -- parenteral --

Column 11, line 52 - "dihloromethane" should be -- dichloromethane --

Column 13, line 42 - "1,4-ethano-b 4,5-dihydroxy-" should be

-- 1,4-ethano-4,5-dihydroxy- --

Signed and Sealed this

Fourteenth Day of June, 1988

Attest:

DONALD J. QUIGG

*Attesting Officer*  *Commissioner of Patents and Trademarks*